Figure 1:
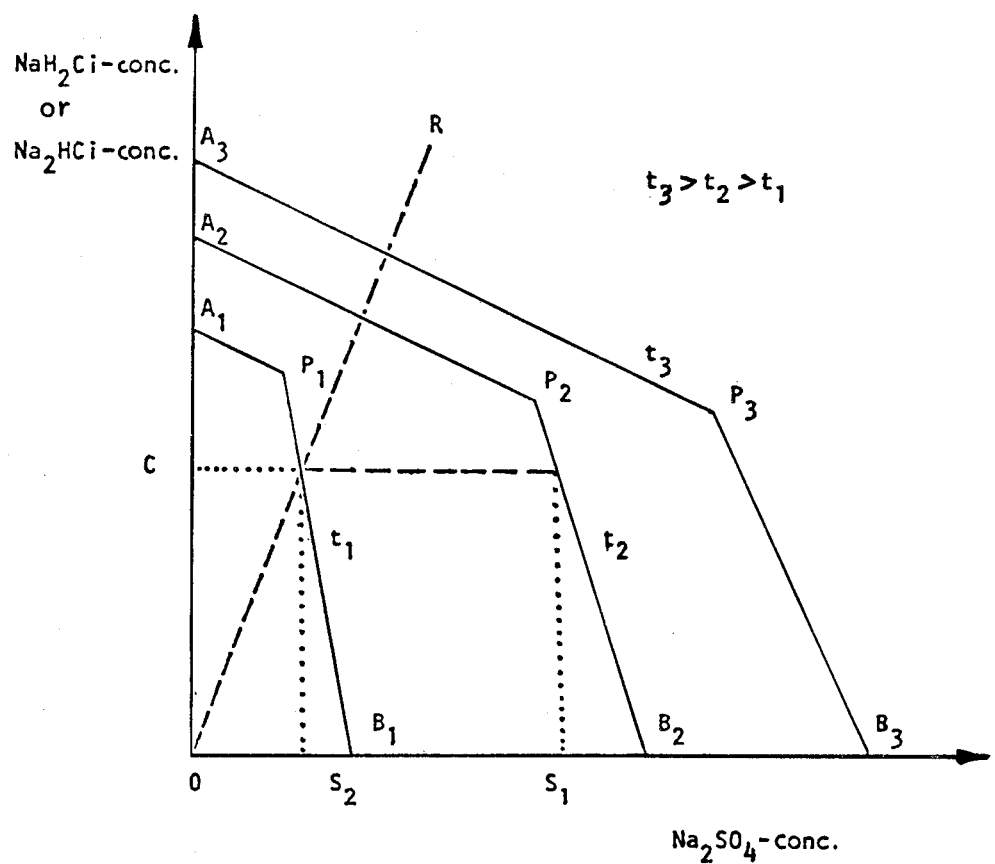

United States Patent [19]

Bengtsson et al.

[11] 4,310,691

[45] Jan. 12, 1982

[54] METHOD FOR SELECTIVELY RECOVERING SODIUM CITRATE FROM AN AQUEOUS SOLUTION

[75] Inventors: Sune Bengtsson, Rowayton; Tom Lillestolen, Fairfield, both of Conn.

[73] Assignee: Aktiebolaget Svenska Flaktfabriken, Nacka, Sweden

[21] Appl. No.: 90,003

[22] Filed: Oct. 31, 1979

[30] Foreign Application Priority Data

Oct. 31, 1978 [SE] Sweden .............................. 7811278

[51] Int. Cl.$^3$ ...................... C07C 59/265; C01B 17/00
[52] U.S. Cl. .................................. 562/584; 562/580; 423/243; 210/737
[58] Field of Search ............... 423/242 A, 242 R, 243, 423/244 A, 244 R, 551; 210/737; 562/580, 584

[56] References Cited

U.S. PATENT DOCUMENTS

| | | | |
|---|---|---|---|
| 2,134,482 | 10/1938 | Johnstone | 423/243 |
| 2,142,987 | 1/1939 | Bacon | 423/539 |
| 3,886,069 | 5/1975 | Trondheim et al. | 210/46 |

FOREIGN PATENT DOCUMENTS

| | | | |
|---|---|---|---|
| 133546 | 5/1974 | Norway | |
| 489745 | 8/1938 | United Kingdom | 423/242 |

OTHER PUBLICATIONS

Vasan, "The Citrex Process for $SO_2$ Removal" Chemical Engineering Progress, vol. 71, No. 5, 1975, pp. 61–66.

Primary Examiner—O. R. Vertiz
Assistant Examiner—Gregory A. Heller
Attorney, Agent, or Firm—Henry H. Skillman

[57] ABSTRACT

A process for recovering sodium citrate from a solution utilized in an absorption/stripping process for $SO_2$ recovery, which involves cooling a portion of the stripping solution to precipitate sodium sulfate, which is separated from the mother liquor. Thereafter, the mother liquor portion is subjected to an evaporative crystallization to precipitate sodium citrate, which is reintroduced along with fresh absorbent solution into the $SO_2$ absorption/stripping process.

11 Claims, 2 Drawing Figures

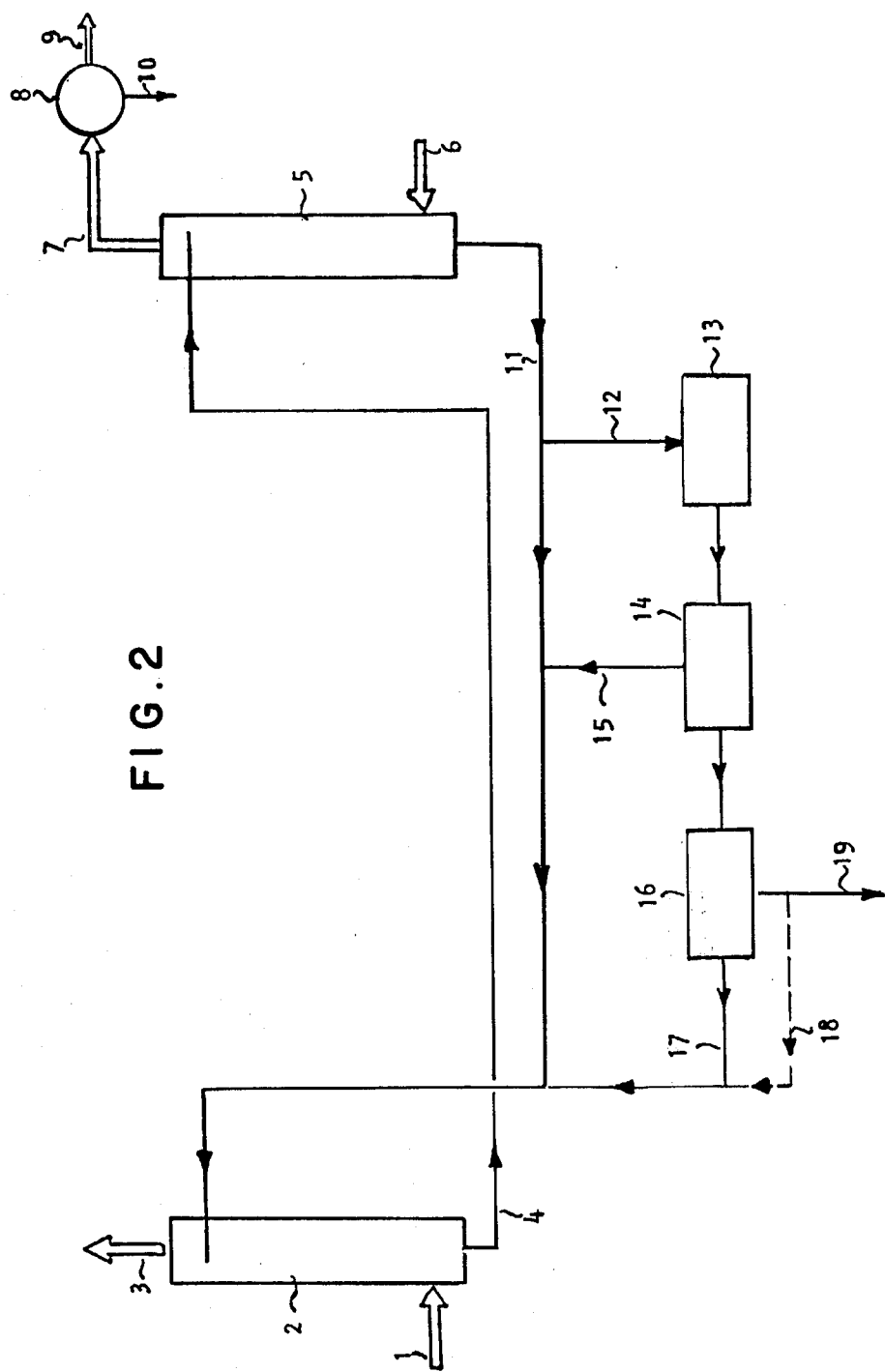

METHOD FOR SELECTIVELY RECOVERING SODIUM CITRATE FROM AN AQUEOUS SOLUTION

This invention relates to a method for selectively recovering sodium citrate from an aqueous solution utilized as the absorption medium in a closed loop absorption/stripping process for the recovery of sulfur dioxide ($SO_2$). As used herein, the expression "closed loop process" is intended to signify a process involving the continuous recirculation of an absorption medium, between the stripper tower and the absorption tower, where the absorption medium is free to absorb new $SO_2$ after having been relieved of $SO_2$ in the stripper tower. In order to enhance the solubility of $SO_2$ in the absorption medium or solution, there is added thereto a substance which is generally referred to, as sodium citrate. This substance can be typically characterized as disodium citrate or monosodium citrate, or a combination of the two. The absorption/stripping process, referred to herein, is utilized for flue gas desulfurization of effluent gases from coal or oil burning power generating plants, off-gases from sulfuric acid plants, Claus-plants and non-ferrous smelters.

In most closed loop processes, there is the potential for the accumulation of undesirable substance which can have a deleterious effect on the process. In the absorption/stripping process referred to herein, the predominant undesirable substance is sodium sulfate. Other sulfur-containing substances, such as thiosulfates and thionates, in addition to sodium chloride and heavy metal salts will also appear, to various extents, and create difficulties in the process. Accordingly, it is extremely important that a method be provided for the economical removal of such undesirable substances. Otherwise, the accumulation of such substances will lead to saturation, causing problems of scaling, in addition to the potential for corrosion due to high accumulation of chlorides.

All industrial off-gases containing $SO_2$, contain some $SO_3$, and possibly some condensed sulfuric acid droplets as well. Furthermore, sulfuric acid is formed from the oxidation, in the liquid phase, of the absorbed $SO_2$. In addition, hydrogen chloride and hydrogen fluoride are absorbed from flue gases containing such species. In order for there to be optimum absorption of $SO_2$, these acidic gas components must be neutralized with the addition of alkali, normally sodium hydroxide or sodium carbonate. As a result, sodium salts are formed, such as sodium sulfate, chloride and fluoride, as described in the following reaction equations:

$$H_2SO_4 + NaOH \rightarrow Na_2SO_4 + 2H_2O \quad (1)$$

$$HCl + NaOH \rightarrow NaCl + H_2O \quad (2)$$

$$HF + NaOH \rightarrow NaF + H_2O \quad (3)$$

In addition to the above, the absorbed $SO_2$ reacts with the dissolved sodium citrate to form sodium bi-sulfite which has the tendency of disproportionation, forming thiosulfates and sulfates:

$$2NaHSO_3 + 2Na_2SO_3 \rightarrow 2Na_2SO_4 + Na_2S_2O_3 + H_2O \quad (4)$$

Furthermore, there may occur the formation of sodium thionate, resulting from the oxidation of sodium bi-sulfite:

$$4NaHSO_3 + O_2 \rightarrow 2Na_2S_2O_6 + 2H_2O \quad (5)$$

The aforementioned reaction products produced in accordance with equations (1)–(5), just like flyash, may be extracted from the stack gases as they pass through the absorber and accumulate in the closed loop system.

The problem exists then, that these substances must be removed from the solution while at the same time assuring minimal losses of the citrate so that the process does not become economically unacceptable.

Methods exist for the removal of sulfates from aqueous solutions. Sulfates can be removed by precipitation and filtering, based on the addition of soluble salts of calcium, barium or strontium. These methods, however, have great disadvantages. Separation by precipitation of $CaSO_4$ can result in excessive losses of citrate due to the formation of the complex calcium citrate, which inactivates the absorbent for $SO_2$ absorption. Utilization of barium as the removal agent, is not practical because it is difficult to recover barium from $BaSO_4$ by any simple means. Strontium has the same disadvantages as Ca and Ba, in addition to the fact that the possibility arises that strontium sulfite may precipitate in the $SO_2$ absorption/stripping loop when soluble strontium salts are used.

Methods utilizing crystallization to remove impurities are complicated by the fact that relatively high concentrations of citrate exist in the absorption/stripping process. As a result there is great risk that co-precipitation or complexing will occur with various of the useful components.

The purpose of the present invention is to provide a new method for the selective separation of these undesirable substances from sodium citrate containing solutions which occur in the absorption/stripping process for $SO_2$ recovery without encountering the aforementioned difficulties. The invention, as described herein, is based on the surprising discovery that sodium sulfate, which represents the most serious of the undesirable substances accumulated in the absorbent solution, can be selectively removed from the absorbent solution. This is accomplished by cooling a slip stream to a given temperature wherein the sodium sulfate can be selectively crystallized and filtered out. This procedure has neither a deleterious effect on the process stream nor results in significant losses due to occlusion and precipitation of sodium citrate. After having selectively removed the sodium sulfate, the sodium citrate can then be selectively crystallized by means of an evaporative crystallization process and removed from the mother liquor.

The remaining mother liquor, which contains, primarily, the accumulated undesireable species and only negligable amounts of sodium sulfate and sodium citrate, can thereafter be discarded. This allows for the maintenance of a prescribed system inventory of these undesirable species. The separated crystalline sodium citrate can then be redissolved and returned to the system. This discovery is a simple method which circumvents the above described problems associated with separation, provides a high degree of recovery of sodium citrate while at the same time allowing for the purging of system contaiminants.

In the following description of the invention Ci is used to designate the citrate anion.

The novel features and advantages of the present invention will become apparent from the following description thereof read in conjunction with the accompanying drawing, in which:

FIG. 1 is a binary solubility phase diagram for the system $Na_2SO_4$-$NaH_2Ci$-$H_2O$ and $Na_2SO_4$-$Na_2HCi$-$H_2O$ at three different temperatures; and FIG. 2 is a schematic illustration of a closed loop absorption/stripping process for the recovery of $SO_2$ employing the selective sodium citrate recovery method of the present invention.

The principle upon which the present invention is based can best be described with reference to FIG. 1. It can readily be seen that the solubility increases with increased temperature. Section $A_1P_1$, $A_2P_2$ and $A_3P_3$ represents the solubility limit for sodium citrate in a sodium sulfate solution. Section $P_1B_1$, $P_2B_2$ and $P_3B_3$ the solubility limit for sodium sulfate in a sodium citrate solution.

The absorption/stripping process discussed herein is characterized by a $Na_2SO_4$ concentration of $S_1$ and a sodium citrate concentration of C, corresponding to the saturation concentration of $Na_2SO_4$ at $t_2$. Cooling a slipstream of this composition to $t_1$, the sodium sulfate will begin to crystallize at $t_2$, whereupon the concentration of sodium sulfate will decrease until a point corresponding to the value $S_2$ is reached, representing a state of equilibrium at temperature $t_1$. The crystals are removed and the mother liquor is evaporated at temperature $t_3$. The concentration of both sulphate and citrate will increase following the line OR, which crosses the solubility curve for sodium citrate, and cause the sodium citrate to crystallize. This can be accomplished in a vacuum crystallizer where the sodium citrate crystallizes and can then be separated, utilizing conventional filtering or centrifugal methods.

The sodium citrate solution which is required for the absorption of $SO_2$ from industrial flue gases generally requires a citrate concentration of from 0.25 to 2.0 gmol/liter, but more typically 0.5 to 1.5 gmol/liter is utilized with a corresponding sulfate concentration of generally about 0.25 to 1.25 gmol/liter, but more typically 0.5 to 1.0 gmol/liter. In the first crystallization cooling step the sulfate concentration is lowered to between 0.15 to 0.6 gmol/liter, or more preferably to between 0.3 to 0.5 gmol/liter. This corresponds to a cooling temperature of about 14° C. or less, and preferably from about 0° to 15° C. The resulting crystal growth is comprised of $Na_2SO_4.10H_2O$, and has been shown to be practically free from any sodium citrate and occlusions of mother liquor, which is indeed surprising. When the precipitate is separated from the mother liquor, it is washed with water, which is then returned to the absorbent to reduce the losses of citrate. The next step, crystallization of sodium citrate by means of evaporation of the mother liquor, and seeding with sodium citrate, is carried out at a temperature of from 40° to 110° C., but more preferably within the range of 50° to 105° C. The amount of water evaporated in this step in at least 80%, but preferably more than 90%. Consequently the majority of the citrate is precipitated and separated from the mother liquor. The mother liquor, which as a result of the above, contains a lower quantity of citrate can be partially returned to the absorbent and the remaining purged. Otherwise, it can be all discharged as waste. This will be a function of the corrosiveness of the fluid which is based on the chloride concentrations in the absorbent circuit.

The incorporation of the present invention into an absorption/stripping process for the recovery of $SO_2$ is shown schematically in FIG. 2. The $SO_2$ laden stack gas stream, indicated by arrow 1, enters adsorption tower 2 and is discharged as a clean gas to the atmosphere 3. The absorbent laden with $SO_2$ is transferred along conduit 4 to the steam stripping tower 5 where the $SO_2$ is stripped from the absorbent with steam, indicated by arrow 6. $SO_2$ and steam, discharged from the stripper, proceed to condensor 8 via conduit 7, wherein the $SO_2$ is concentrated and discharged at 9. The water condenses and leaves in conduit 10.

The $SO_2$ lean absorbent can now be returned to the absorber via conduit 11 for absorption of new $SO_2$. A small purge stream, normally 0.1 to 5% of the recirculation flow in conduit 11 is removed via conduit 12 and is sent to cooler 13 where the sodium sulfate is separated. Sodium sulfate precipitates and the mother liquor is discharged to a separator 14 which can be either a filter or a centrifuge. The water used to wash the crystals after separation is returned to the absorbent via stream 15. The mother liquor is then sent to an evaporator which can be the same vessel as the cooler, above, 13 or to an evaporator crystallizer 16. Here the sodium citrate is precipitated and returned to the absorber via stream 17 in the crystalline or dissolved form. From the evaporator crystallizer the mother liquor can either be totally discarded at 19, or part of it returned to the process via stream 18. It should be noted that this process can be operated either continuously or on a batch basis.

EXAMPLE

A typical absorption/stripping process for $SO_2$ recovery handles 100,00 Nm 3/h flue gas, containing 0.3% (v) $SO_2$, 0.002% (v) $SO_3$ and 0.0004% (v) HCl. The absorbent was comprised of a sodium citrate solution having the following composition in mass/$m^3$ solution:

|  |  |
|---|---|
| $NaH_2Ci$ | 107 kg/$m^3$ |
| NaHCi | 118 kg/$m^3$ |
| $Na_2SO_4$ | 100 kg/$m^3$ |
| NaCl | 3.3 kg/$m^3$ |
| $Na_2S_2O_3$ | 1 kg/$m^3$ |
| $Na_2S_2O_6$ | 2 kg/$m^3$ |
| $H_2O$ | 590 kg/$m^3$ |
| Remainder | 3.7 kg/$m^3$ |
| Density | 1150 kg/$m^3$ |

The circulation rate between the absorber and stripper was 170 $m^3$/h. Sodium sulfate was produced in the absorber at a rate of 31.7 kg/h in combination with NaCl which was produced at a rate of 1.04 kg/h. From a corrosion point of view it was desired to maintain the chloride concentration at 2000 ppm in the circulation stream. Therefore the purge rates for treatment and recovery of sodium citrate were taken as 0.459 $m^3$/h, which is approximately 0.3% of the circulation flow. This slip stream was cooled to 7° C. in a cooling crystallizer where 71.9 kg/h $Na_2SO_4.10H_2O$ was crystallized. This corresponds to 69% of the dissolved sodium sulfate. The crystal mass, was then separated and washed and the wash water was returned to the absorber. Analysis of the crystalline discharge showed that approximately 0.10 kg citric acid was lost, which corresponds to about 0.11% of the original sodium citrate. The mother liquor from the cooling stage was evaporated at a temperature of 80° C., whereupon the sodium citrate began to crystallize.

The crystalline precipitate was separated and returned to the absorbent, whereupon the remaining mother liquor was slowly cooled to 35° C. Seed crystals of sodium citrate may be added to cause futher crystallization and thereby enchance its recovery. The remaining mother liquor, a scant 20 kg/h was purged as waste, which included all the undesireable components. Citric acid in this mother liquor was analyzed as a 0.12 kg/kg solution and corresponded to 2.7% of the slip stream citrate content. Therefore, it can be seen that 97.2% of the citrate was recovered in this process corresponding to a total loss of citric acid of just 2.5 kg/h. This is considered an extremely low loss. Furthermore, this loss can be reduced assuming the raw gas holds lower concentrations of HCl and $SO_3$.

We claim:

1. A process for recovering sodium citrate from the spent absorbent solution utilized in an absorption/stripping process for $SO_2$ recovery, which comprises
   a. cooling a portion of said spent absorbent solution to a temperature of about 14° C. or less, thereby causing precipitation of sodium sulfate present in said portion of absorbent solution;
   b. separating the sodium sulfate precipitate from said portion of absorbent solution;
   c. heating said portion of absorbent solution from which said sodium sulfate has been separated to a temperature of at least 40° C. to evaporate water and reduce the volume thereof sufficiently to cause precipitation of the sodium citrate contained therein; and
   d. separating the precipitated sodium citrate from said portion of absorbent solution.

2. The process according to claim 1 wherein said cooling step cools said portion of spent absorbent solution to a temperature of about 5° to 10° C.

3. The process according to claims 1 or 2 wherein said heating step heats said portion of absorbent solution to a temperature of about 50° to 105° C.

4. The process according to claim 1 wherein said heating step heats said portion of absorbent solution sufficiently to reduce its volume to less than 20% of its original volume.

5. The process according to claim 1 wherein said heating step heats said portion of absorbent solution sufficiently to reduce its volume to less than 10% of its original volume.

6. The process according to claim 1 or 2 wherein the absorbent solution remaining from step (d) is cooled to about 25° C. to 40° C. to precipitate additional sodium citrate, and said additional sodium citrate is separated from said portion of stripping solution.

7. The process according to claim 6 wherein cooling of said absorbent solution occurs over a period from about 20 minutes of 2 hours.

8. The process according to claim 6 including disposing of said portion of absorbent solution after separation of said additional sodium citrate.

9. The process according to claims 1 or 6 including introducing the separated sodium citrate with fresh absorbent solution together into the said absorption/stripping process for $SO_2$.

10. The process according to claim 1 wherein the cooling step and heating step are carried out in the same vessel.

11. The process according to claim 1 including disposing of the portion of absorbent solution from which the sodium citrate has been separated.

* * * * *